(12) United States Patent
Tagawa (10) Patent No.: US 10,058,294 B2
(45) Date of Patent: Aug. 28, 2018

(54) RADIATION IMAGING SYSTEM COMPRISING A PLURALITY OF RADIATION IMAGING DEVICES AND A PLURALITY OF RETAINERS CONFIGURED TO POSITION AND RETAIN THE PLURALITY OF RADIATION IMAGING DEVICES

(71) Applicant: CANON KABUSHIKI KAISHA, Tokyo (JP)

(72) Inventor: Motoki Tagawa, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 254 days.

(21) Appl. No.: 15/006,915

(22) Filed: Jan. 26, 2016

(65) Prior Publication Data

US 2016/0220202 A1 Aug. 4, 2016

(30) Foreign Application Priority Data

Jan. 30, 2015 (JP) ................................. 2015-017883
Aug. 20, 2015 (JP) ................................. 2015-162919

(51) Int. Cl.
*A61B 6/00* (2006.01)
*A61B 6/10* (2006.01)

(52) U.S. Cl.
CPC .......... *A61B 6/4266* (2013.01); *A61B 6/4208* (2013.01); *A61B 6/4233* (2013.01); *A61B 6/4283* (2013.01); *A61B 6/4452* (2013.01); *A61B 6/5241* (2013.01); *A61B 6/5258* (2013.01); *A61B 6/107* (2013.01); *A61B 6/4429* (2013.01); *A61B 6/54* (2013.01); *A61B 6/585* (2013.01)

(58) Field of Classification Search
CPC ... A61B 6/4233; A61B 6/4266; A61B 6/5241; A61B 6/4208; A61B 6/4283; A61B 6/4429; A61B 6/4452; A61B 6/54
USPC ................. 378/98.8, 98.12, 189; 250/370.09
See application file for complete search history.

(56) References Cited

U.S. PATENT DOCUMENTS 5,473,664 A * 12/1995 Strawder .............. G03B 42/025
378/167
6,269,177 B1 7/2001 Dewaele et al.
(Continued)

FOREIGN PATENT DOCUMENTS

CN 102204826 A 10/2011
CN 102379708 A 3/2012
(Continued)

*Primary Examiner* — Allen C. Ho
(74) *Attorney, Agent, or Firm* — Canon USA Inc., IP Division (57) ABSTRACT

A radiation imaging system includes a housing containing a plurality of radiation imaging devices each including a radiation detecting panel having a two-dimensional matrix of pixels and arranged to convert applied radiation to an image signal, a plurality of retainers configured to position and retain the plurality of radiation imaging devices so that parts of the respective radiation imaging devices spatially overlap as viewed from an irradiation side, and a unit configured to acquire a radiographic image on the basis of image signals from the respective radiation imaging devices. The plurality of retainers are configured to retain the plurality of radiation imaging devices in areas other than effective pixel areas of the respective radiation imaging devices.

20 Claims, 9 Drawing Sheets

(56) References Cited

U.S. PATENT DOCUMENTS

| | | | |
|---|---|---|---|
| 6,273,606 B1* | 8/2001 | Dewaele | A61B 6/5241 378/174 |
| 6,403,964 B1 | 6/2002 | Kyyhkynen | |
| 6,592,257 B1* | 7/2003 | Heidsieck | A61B 6/502 378/189 |
| 6,614,032 B2* | 9/2003 | Wendlandt | G03B 42/025 206/455 |
| 6,696,691 B2* | 2/2004 | Foos | G03B 42/047 250/484.4 |
| 6,744,062 B2* | 6/2004 | Brahm | G03B 42/02 250/584 |
| 6,793,390 B2* | 9/2004 | Wang | G06T 3/0075 378/174 |
| 7,108,421 B2* | 9/2006 | Gregerson | A61B 6/032 378/146 |
| 7,144,158 B2* | 12/2006 | Dippl | G03B 42/02 378/177 |
| 7,247,858 B2* | 7/2007 | De Keyser | A61B 6/00 250/370.01 |
| 7,498,583 B2* | 3/2009 | Shoji | A61B 6/4266 250/370.09 |
| 7,575,373 B2* | 8/2009 | Xu | A61B 6/00 378/169 |
| 7,581,883 B2* | 9/2009 | Kato | G03B 42/02 378/167 |
| 7,650,044 B2* | 1/2010 | Kreang-Arekul | G06T 3/4038 382/128 |
| 7,775,712 B1* | 8/2010 | Thieman | G03B 42/04 378/186 |
| 7,828,481 B2* | 11/2010 | Ye | A61B 6/0457 378/117 |
| 7,857,511 B2* | 12/2010 | Hesl | A61B 6/4233 378/189 |
| 7,869,564 B2* | 1/2011 | Kalender | G06T 7/12 378/37 |
| 7,909,511 B2* | 3/2011 | Hall | A61B 6/4233 378/189 |
| 7,988,356 B2* | 8/2011 | Watanabe | A61B 6/00 378/189 |
| 8,182,147 B2* | 5/2012 | Nishino | A61B 6/00 378/189 |
| 8,186,879 B2* | 5/2012 | Li | A61B 6/4283 378/189 |
| 8,325,875 B2* | 12/2012 | Omernick | A61B 6/42 378/62 |
| 8,344,327 B2* | 1/2013 | Yamaguchi | A61B 6/5241 250/363.07 |
| 8,351,568 B2* | 1/2013 | Minnigh | A61B 6/4266 378/204 |
| 8,360,639 B2* | 1/2013 | Kato | A61B 6/4233 378/197 |
| 8,461,543 B2* | 6/2013 | Nishino | A61B 6/548 250/370.08 |
| 8,485,726 B2* | 7/2013 | Kobayashi | A61B 6/4233 250/370.09 |
| 8,586,934 B2* | 11/2013 | Nakatsugawa | G01T 1/2985 250/363.02 |
| 8,616,766 B2* | 12/2013 | Takahashi | G03B 42/04 378/189 |
| 8,625,742 B2* | 1/2014 | Iwashita | A61B 6/4266 378/116 |
| 8,714,817 B2* | 5/2014 | Oyaizu | G03B 42/047 378/189 |
| 8,723,131 B2* | 5/2014 | Kobayashi | G03B 42/02 250/370.01 |
| 8,748,834 B2* | 6/2014 | Enomoto | A61B 6/4233 250/370.08 |
| 8,834,022 B2* | 9/2014 | Koyanagi | A61B 6/56 250/370.09 |
| 8,848,872 B2* | 9/2014 | Lee | A61B 6/4494 250/370.09 |
| 8,851,750 B2* | 10/2014 | Lee | G03B 42/04 378/189 |
| 8,899,832 B2* | 12/2014 | Fabrizio | A61B 6/08 378/195 |
| 8,956,045 B2* | 2/2015 | Tajima | A61B 6/4283 378/145 |
| 9,016,940 B2* | 4/2015 | Fabrizio | A61B 6/02 378/177 |
| 9,168,011 B2* | 10/2015 | Nenoki | A61B 6/4283 |
| 9,204,855 B2* | 12/2015 | Tsubota | H04W 76/10 |
| 9,265,467 B2* | 2/2016 | Kamiya | A61B 6/5241 |
| 9,402,592 B2* | 8/2016 | Garcia | A61B 6/4283 |
| 9,405,183 B2* | 8/2016 | Ando | A61B 6/4266 |
| 9,412,257 B2* | 8/2016 | Tajima | G08B 13/22 |
| 9,414,802 B2* | 8/2016 | Urbon | A61B 6/4283 |
| 9,462,982 B2* | 10/2016 | Suzuki | A61B 6/4283 |
| 9,492,137 B2* | 11/2016 | Iwamoto | A61B 6/4283 |
| 9,521,983 B2* | 12/2016 | Jang | A61B 6/4429 |
| 9,535,176 B2* | 1/2017 | Miyoshi | G01T 7/00 |
| 9,538,978 B2* | 1/2017 | Makino | G16H 40/63 |
| 9,541,509 B2* | 1/2017 | Akahori | A61B 6/486 |
| 9,655,575 B2* | 5/2017 | Park | A61B 6/4233 |
| 9,668,706 B2* | 6/2017 | Kim | A61B 6/563 |
| 9,675,309 B2* | 6/2017 | Kim | A61B 6/4266 |
| 9,700,271 B2* | 7/2017 | Horiuchi | A61B 6/4405 |
| 9,810,001 B2* | 11/2017 | Bostley | E05B 65/006 |
| 2006/0219926 A1 | 10/2006 | Shoji et al. | |
| 2010/0080348 A1 | 4/2010 | Kalender et al. | |
| 2011/0049343 A1 | 3/2011 | Yamaguchi | |
| 2011/0057111 A1 | 3/2011 | Nishino | |
| 2013/0083898 A1 | 4/2013 | Tajima et al. | |
| 2014/0177804 A1 | 6/2014 | Kobayashi et al. | |

FOREIGN PATENT DOCUMENTS

| | | |
|---|---|---|
| CN | 105997109 A | 10/2016 |
| DE | 20120165 U1 | 4/2002 |
| JP | H11-244270 A | 9/1999 |
| JP | 2002-336225 A | 11/2002 |
| JP | 2011-224340 A | 11/2011 |
| JP | 2012-040140 A | 3/2012 |
| JP | 2012-229999 A | 11/2012 |
| JP | 2013-081768 A | 5/2013 |
| RU | 2187244 C1 | 8/2002 |

* cited by examiner

RADIATION IMAGING SYSTEM COMPRISING A PLURALITY OF RADIATION IMAGING DEVICES AND A PLURALITY OF RETAINERS CONFIGURED TO POSITION AND RETAIN THE PLURALITY OF RADIATION IMAGING DEVICES

BACKGROUND OF THE INVENTION

Field of the Invention

The present invention relates to a radiation imaging system applied to medical diagnostic imaging apparatuses, non-destructive inspection apparatuses, and analyzers using radiation.

Description of the Related Art

In recent years, for example, in the field of medicine, there has been a demand for photographing an observed area with a long length (hereinafter referred to as long-length photographing). For example, photographing of the entire spinal cord or lower limb or of the entire body, for identifying distortion of, or abnormalities in, the subject's body. A radiation imaging system capable of long-length photographing in a single irradiation is more desirable than a system that performs long-length photographing in multiple irradiations of an observed area which is divided into multiple sections. This is because, with the former system, the subject's body movement can be avoided and the subject's exposure to radiation can be reduced.

Japanese Patent Laid-Open No. 2012-040140 and Japanese Patent Laid-Open No. 11-244270 each disclose a radiation imaging system that can perform long-length photographing in a single irradiation by using a plurality of radiation imaging devices, which are arranged such that parts of the respective radiation imaging devices spatially overlap as viewed from an irradiation side. Japanese Patent Laid-Open No. 11-244270 discloses a supporting member for arranging the radiation imaging devices such that parts of the respective radiation imaging devices spatially overlap as viewed from the irradiation side.

However, in Japanese Patent Laid-Open No. 2012-040140, there is no mention of a retainer that retains the position of each of the radiation imaging devices. Also, Japanese Patent Laid-Open No. 11-244270 does not describe a specific configuration of a retainer that retains the position of each of the radiation imaging devices. Depending on the configuration of the retainer that retains the position of each of the radiation imaging devices, artifacts may occur in an image obtained from the radiation imaging system.

SUMMARY OF THE INVENTION

Accordingly, an aspect of the present invention provides a technique advantageous in reducing artifacts which may occur in an image due to the presence of a retainer that retains the position of each of radiation imaging devices.

A radiation imaging system according to an aspect of the present invention includes a housing containing a plurality of radiation imaging devices each including a radiation detecting panel having a two-dimensional matrix of pixels and arranged to convert applied radiation to an image signal, a plurality of retainers configured to position and retain the plurality of radiation imaging devices so that parts of the respective radiation imaging devices spatially overlap as viewed from an irradiation side, and a unit configured to acquire a radiographic image on the basis of image signals from the respective radiation imaging devices. The plurality of retainers are configured to retain the plurality of radiation imaging devices in areas other than effective pixel areas of the respective radiation imaging devices.

Further features of the present invention will become apparent from the following description of embodiments with reference to the attached drawings.

DESCRIPTION OF THE EMBODIMENTS

Embodiments of the present invention will now be specifically described with reference to the attached drawings. Dimensions and detailed structures shown in the embodiments are not limited to those in the present description and drawings. In the present specification, the term radiation includes not only X-rays, but also α-rays, β-rays, γ-rays, corpuscular rays, and cosmic rays.

Figure 1:
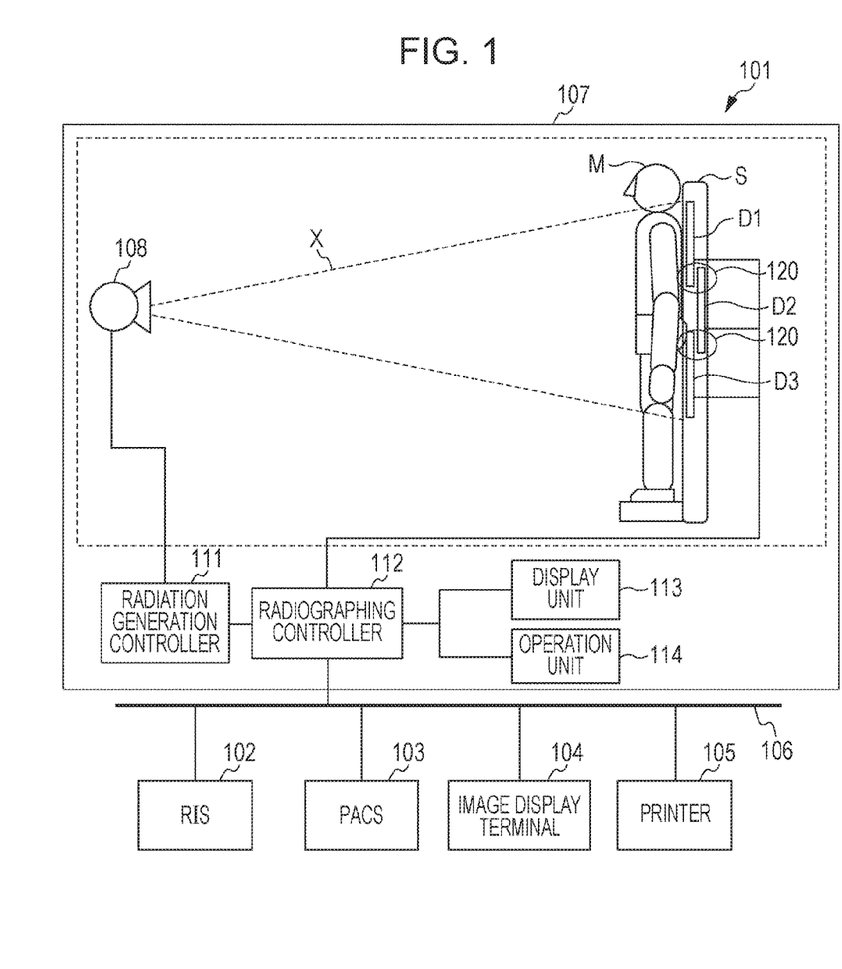
FIG. 1 is a schematic cross-sectional view for explaining a medical diagnostic system according to an aspect of the present invention.

A medical diagnostic system will now be described with reference to FIG. 1. FIG. 1 is a schematic cross-sectional view for explaining a medical diagnostic system.

A medical diagnostic system 101 includes a radiology information system (RIS) 102, a picture archiving and communication system (PACS) 103, a diagnostic image display terminal 104, a printer 105, and a radiographing system 107. These components are connected to one another via a communication medium 106, such as a network.

The RIS 102 is a system that carries out management from reservations for radiological examinations and treatments to examination results. This system may be, for example, an information management system for overall management of information that accompanies radiographic images or examination orders (instructions). The accompanying information may contain examination information, including examination IDs or receipt numbers. The operator can input an examination order through the RIS 102. The radiographing system 107 performs photographing in accordance with the input examination order. In the present embodiment, the input examination order is stored and managed by the RIS 102. However, the input examination order may be stored and managed by a server (not shown) connected to the RIS 102 and the radiographing system 107. As another embodiment, the input examination order may be stored and managed by the radiographing system 107.

The PACS 103 stores and manages radiographic digital images (hereinafter referred to as photographed images) photographed by the radiographing system 107. That is, the PACS 103 may serve as part of an image management system that manages photographed images. The diagnostic image display terminal 104 is capable of displaying a photographed image stored in the PACS 103. The printer 105 is capable of printing a photographed image stored in the PACS 103.

The radiographing system 107 performs examination (photographing) on the basis of an examination order, including a plurality of pieces of examination information. The examination information includes photographing protocol information. Each of photographing protocols defines photographing conditions or the types of image processing to be performed on the photographed image. More specifically, the photographing protocols include parameter information or photographing implementation information used for performing photographing or image processing, and photographing environment information, such as a sensor type or photographing position. The examination information also includes information, such as an examination ID and a receipt number, for identifying the examination order, or for identifying the photographed image based on the examination order.

The radiographing system 107 includes a radiation imaging system S, a radiation source 108, a radiation generation controller 111, a radiographing controller 112, a display unit 113, and an operation unit 114. The radiation imaging system S includes a first radiation imaging device D1, a second radiation imaging device D2, and a third radiation imaging device D3. The radiation source 108 functions as a radiation generator. That is, the radiation source 108 is an X-ray tube in the present embodiment, and applies radiation (which is X-rays here) to an object to be photographed (i.e., subject to be examined). Each of the radiation imaging devices D1, D2, and D3 includes a radiation detecting panel 2 (see FIG. 9A) having a two-dimensional matrix of pixels and configured to convert the applied radiation to an image signal, and performs imaging on the basis of the radiation transmitted through the subject. A sensor for converting the radiation into an electric, signal may be a direct conversion sensor (e.g., a-Se sensor) that directly converts the radiation to an electric signal, or an indirect conversion sensor using a scintillator (e.g., CsI) and a photoelectric conversion element. The radiation imaging devices D1, D2, and D3 each perform analog-to-digital (A/D) conversion of the resulting electric signal to generate a photographed image, which is radiographic image data, and transfer the photographed image to the radiographing controller 112.

In the system illustrated in FIG. 1, the first radiation imaging device D1 and the third radiation imaging device D3 are disposed closer to the radiation source 108 (i.e., irradiation side) than the second radiation imaging device D2 is. The first radiation imaging device D1 and the third radiation imaging device D3 are arranged such that each of their respective parts spatially overlaps the corresponding part of the second radiation imaging device D2, as viewed from the irradiation side. The spatially overlapping may mean either being physically in contact, or overlapping at a distance without physical contact. With this overlapping area 120, it is possible to synthesize images. In the area 120, the structure of the radiation imaging device D1 or D3 disposed on the irradiation side is noticeably reflected on the second radiation imaging device D2, and this causes quality degradation in part of the resulting image. The overlapping radiation imaging devices D1, D2, and D3 on upper, middle, and lower levels, respectively, are arranged on the front, back, and front sides in this order, so that an increase in enlargement ratio at upper and lower ends can be reduced. The configuration of the radiation imaging system S will be described in detail later on.

In accordance with control by the radiographing controller 112, the radiation generation controller 111 controls generation of radiation on the basis of a photographing protocol. Specifically, in accordance with photographing conditions (e.g., parameters, such as tube current, tube voltage, and irradiation time) corresponding to the photographing protocol, the radiation generation controller 111 applies a voltage to the radiation source 108 to cause it to generate radiation.

The radiographing controller 112 controls overall radiographing processing based on the photographing protocol. The radiographing controller 112 also performs image processing on the photographed image obtained from the radiation imaging system S. The image processing includes synthesis of a plurality of photographed images from the radiation imaging devices D1 to D3, correction, gradation processing, and frequency processing. The radiographing controller 112 performs the image processing using image processing parameters corresponding to the photographing protocol. The radiographing controller 112 is capable of transmitting the resulting photographed image to an external device, such as the PACS 103 or printer 105. The PACS 103 stores the transmitted photographed image, together with examination information for identifying the photographed image. The examination information may be, for example, an examination ID or receipt number assigned to the examination order. The PACS 103 may store the examination order while associating it with the photographed image.

The display unit 113 displays information, such as a system state, to the operator. For example, the display unit 113 may be a display device. The display unit 113 is capable of displaying, for example, an examination order received from the RIS 102 or created by the operator of the radiographing system 107. The operation unit 114 acquires an instruction from the operator. For example, the operation unit 114 may be a keyboard, a mouse, or various buttons. The operator can input, for example, an image duplication instruction to the radiographing system 107 using the operation unit 114.

Figure 2A:
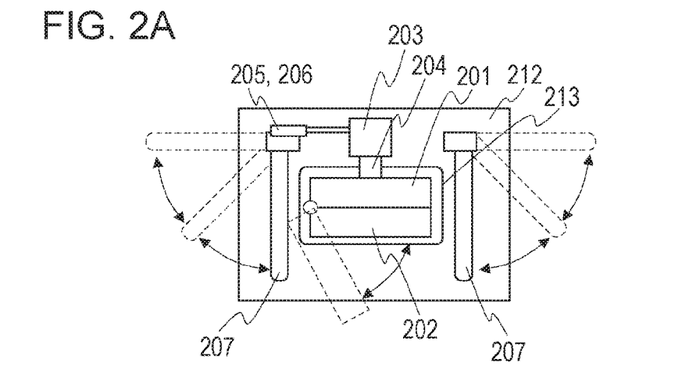
FIGS. 2A to 2C illustrate an external structure of a radiation imaging system according to an aspect of the present invention.
Figure 2B:
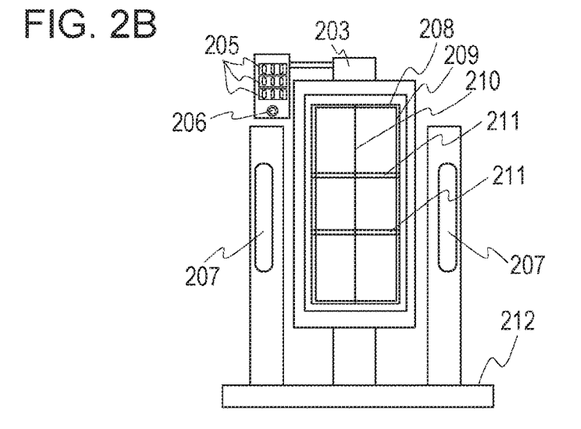
Figure 2C:
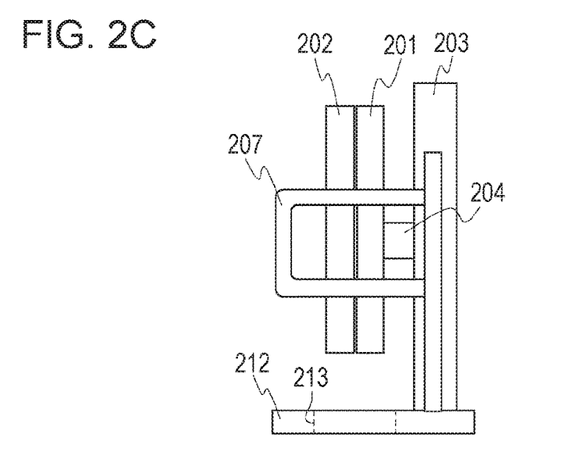

FIGS. 2A to 2C illustrate an external structure of the radiation imaging system S illustrated in FIG. 1. FIG. 2A is a top view, FIG. 2B is a front view, and FIG. 2C is a side view.

The radiation imaging devices D1 to D3 are contained in a housing including a container 201 and a door unit 202. The door unit 202, which can he opened and closed, is provided on the front side of the container 201. Opening and closing the door unit 202 allows the radiation imaging devices D1 to D3 to be removed from or mounted in the housing of the radiation imaging system S. If the radiation imaging devices D1 to D3 are transportable, the radiation imaging devices D1 to D3 can be mounted in the housing of the radiation imaging system S for use in long-length photographing, and can be removed from the housing of the radiation imaging system S for use in other purposes. Better usability can thus be achieved.

Indices 208 to 211 for use in X-ray photographing are shown on the front side of the door unit 202. The index 208 indicates an effective photographing area where radiographing is possible, as perpendicularly viewed from the radiation source 108. The index 209 indicates a photographable area which takes into account an enlargement ratio when the radiation source 108 is positioned such that radiation is perpendicularly incident on the center of the effective photographing area. A radiation detection surface is distant from the front side of the door unit 202. Therefore, when the enlargement ratio is taken into account, the area of a photographed image actually obtained is smaller than the area indicated by the index 208. In particular, since an area with a long length in the longitudinal direction is to be photographed, an actual photographable area is significantly different from the range indicated by the index 208 in the longitudinal direction. The index 209 is thus effective for long-length photographing. The index 210 indicates the center in the direction along short sides of the effective area. Since the door unit 202 includes a grid for eliminating scattered radiation, the radiation source 108 needs to be positioned such that radiation is perpendicularly incident on the center line indicated by the index 210. The indices 211 each indicate the area 120 where two of the radiation imaging devices D1 to D3 included in the radiation imaging system S overlap each other. As described above, the area 120 is an area where image quality is degraded. Therefore, when there is a portion for which a high-quality image is required, the positional relationship between the subject and the container 201 needs to be adjusted such that this portion is not located in the area 120. The indices 211 are used for this adjustment.

The container 201 is held by a supporting column 203, with a connecting portion 204 interposed therebetween. A drive unit included in the supporting column 203 can move the container 201 up and down via the connecting portion 204. The supporting column 203 has state indicators 205 indicating the states of the respective radiation imaging devices D1 to D3, and an emergency stop portion 206 for stopping the up-and-down movement of the container 201. For each of the radiation imaging devices D1 to D3 included in the radiation imaging system S, the corresponding state indicator 205 indicates, for example, the presence or absence in the container 201, the state of power source, the state of photographing operation, and the state of communicating operation. The three state indicators 205 are longitudinally arranged to indicate the respective states of the radiation imaging devices D1, D2, and D3, in this order from the top, to allow an intuitive understanding of which radiation imaging device is in what state. If the container 201 moves up and down in an unexpected way, the up-and-down movement can be stopped by pressing the emergency stop portion 206. The container 201 is provided with handles 207 on both sides thereof. The handles 207 are provided to support the subject who cannot stand during photographing. The handles 207 each have an opening in the center thereof. Each of the radiation imaging devices D1 to D3 may be laterally passed through the opening to be mounted in the container 201. The handles 207 are configured to be pivotable and retractable to both sides, so as not to cause an obstruction during opening and closing of the door unit 202 or mounting of the radiation imaging devices D1 to D3. The supporting column 203 and the handles 207 are attached to a table 212, on which the subject is X-ray photographed. The table 212 has an opening 213 below the container 201 and the door unit 202. When the container 201 is lowered and inserted into the opening 213, an effective photographing area can extend to a position below the upper surface of the table 212. This allows photographing of a distal end of the subject's foot on the table 212.

Figure 9A:
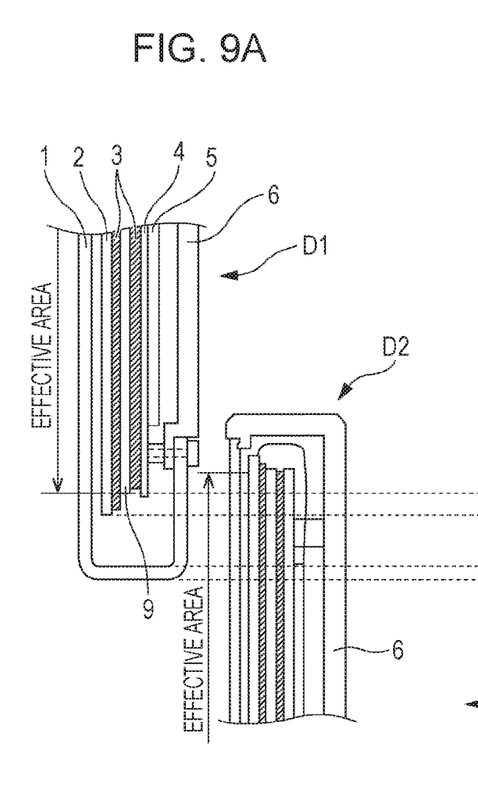
FIGS. 9A and 9B illustrate a cross-sectional structure of radiation imaging devices and values of image signals, according to an aspect of the present invention.
Figure 9B:
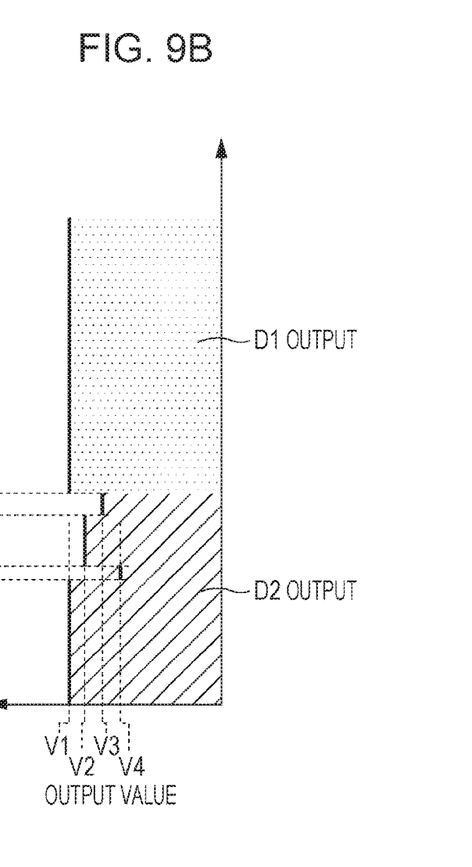

A structure of the first radiation imaging device D1 will now be described with reference to FIGS. 9A and 9B. FIG. 9A is an enlarged schematic cross-sectional view of a circled portion in FIG. 1, and FIG. 9B is a conceptual diagram illustrating image signals in this portion. In FIG. 9B, "output value" represents the value of an image signal based on radiation that can reach the radiation detecting panel 2 of each of the radiation imaging devices D1 and D2. Also in FIG. 9B, "D1 output" represents the value of an image signal from the first radiation imaging device D1, and "D2 output" represents the value of an image signal from the second radiation. imaging device D2. An image signal V1 in "D2 output" represents the value of an image signal based on radiation that reaches the second radiation imaging device D2 without passing through the first radiation imaging device D1. Image signals V2 to V4 each represent the value of an image signal based on radiation that passes through at least part of the first radiation imaging device D1 and reaches the second radiation imaging device D2. The image signal V4 represents the value of an image signal based on radiation that passes through an end portion of a first member 1 of the first radiation imaging device D1. The image signal V2 represents the value of an image signal based on radiation that passes through a flat portion of the first member 1 of the first radiation imaging device D1. The image signal V3 represents the value of an image signal based on radiation that passes through an area outside an effective pixel area in the radiation detecting panel 2 of the first radiation imaging device D1.

As illustrated in FIGS. 9A and 9B, each of the radiation imaging devices D1 and D2 includes the radiation detecting panel 2, an adhesive 3, a radiation shielding member 9, an adhesive 3, a base 4, and a printed circuit board 5 stacked in this order from the irradiation side and contained in the housing of the radiation imaging device. The radiation detecting panel 2 is bonded with the adhesive 3 to the radiation shielding member 9 and then to the base 4. This allows the radiation detecting panel 2 to be supported by the base 4. The printed circuit board 5 is disposed opposite the radiation detecting panel 2, with the base 4 interposed therebetween.

The housing of each of the radiation imaging devices D1 and D2 includes the first member 1 and a second member 6. The first member 1 may be made of a material with radiability of 5 mm aluminum equivalent or less from the radiation incident direction. For example, carbon-fiber-reinforced plastic (CFRP) is used as the material of the first member 1. In the first member 1, radiation transmittance in an area facing the effective pixel area in the radiation detecting panel 2 (described below) may be higher than that in the other area. In the housing of the second radiation imaging device D2, the second member 6 forming an area facing an integrated circuit (IC) may be made of CFRP, but is preferably made of a material with higher rigidity and lower specific gravity than the first member 1. A metal material, such as aluminum or magnesium, is used to form the second member 6.

The radiation detecting panel 2 has a plurality of pixels arranged in a two-dimensional matrix. The radiation detecting panel 2 has an effective pixel area (corresponding to "effective area" in FIG. 9A) where radiation can be captured, and an area outside the effective pixel area. In one of the areas 120 (see FIG. 1 and FIG. 4B), the effective pixel areas of the first radiation imaging device D1 and the second radiation imaging device D2 are arranged to spatially overlap each other, as viewed from the irradiation side.

The radiation shielding member 9 is a sheet member containing lead (Pb) or tungsten (W) with a high radiation absorbed dose. The radiation shielding member 9 is used for protection of an IC in the printed circuit board 5, and for shielding against radiation transmitted through each radiation imaging device and scattered by the wall of the photographing room or the like. The radiation shielding member 9, which has a high radiation absorbed dose, acts not to allow radiation from the radiation source 108 to pass through the back side of the first radiation imaging device D1. As a result, depending on the position of the radiation shielding member 9, radiation to be used for imaging in the second radiation imaging device D2 may be blocked by the radiation shielding member 9 of the first radiation imaging device D1. That is, the values of some image signals from the second radiation imaging device D2 may be smaller than that of the image signal V1 in FIG. 9B, due to the presence of the radiation shielding member 9. Therefore, the radiation shielding member 9 of the first radiation imaging device D1 is disposed not to overlap the effective pixel area of the second radiation imaging device D2 as viewed from the irradiation side. At the same time, the radiation shielding member 9 of the first radiation imaging device D1 is disposed to be located within the effective pixel area of the first radiation imaging device D1 as viewed from the irradiation side.

With this configuration, since the effective pixel area of the second radiation imaging device D2 and the radiation shielding member 9 of the first radiation imaging device D1 do not spatially overlap, the undesired absorption of radiation by the radiation shielding member 9 is reduced. Thus, it is possible to suppress artifacts which may occur, due to the presence of the radiation shielding member 9 of the first radiation imaging device D1, in an image obtained from the second radiation imaging device D2.

The relationship between the first radiation imaging device D1 and the second radiation imaging device D2 has been described above, and the same applies to the relationship between the third radiation imaging device D3 and the second radiation imaging device D2. That is, the radiation shielding member of the radiation imaging device on the front side, as viewed from the irradiation side, is disposed not to spatially overlap the effective pixel area of the radiation imaging device on the back side, as viewed from the irradiation side. Thus, in long-length photographing, artifacts which may occur in an image obtained from the radiation imaging device on the back side can be suppressed.

Figure 3A:
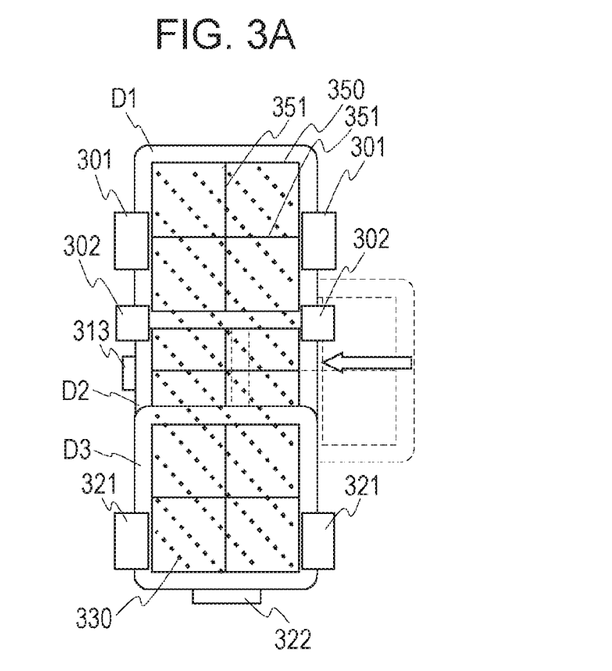
FIGS. 3A and 3B illustrate a mounted state of radiation imaging devices according to an aspect of the present invention.
Figure 3B:
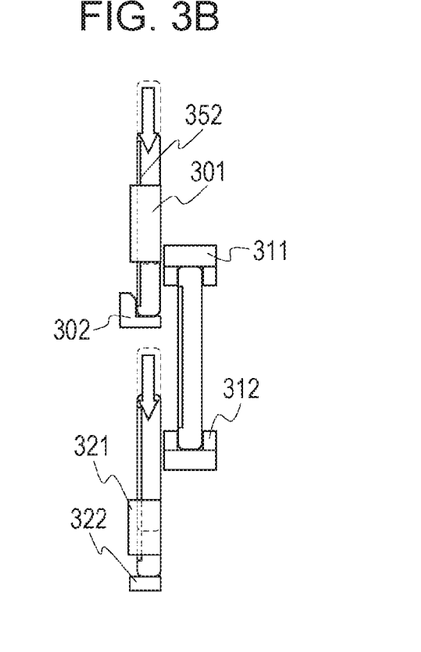

FIGS. 3A and 3B illustrate a mounted state of the radiation imaging devices D in the container 201. FIG. 3A is a front view, and FIG. 3B is a side view.

Each of the radiation imaging devices D1 to D3 has, on the front side thereof, an index 350 indicating an effective area where radiographing is possible, and an index 351 indicating the center of the effective area. Each of the radiation imaging devices D1 to D3 also has, on the side thereof, an index 352 indicating an effective area where radiographing is possible. By performing synthesis after photographing with the radiation imaging devices D1, D2, and D3 overlapping one another, a photographed image, which is a radiographic digital image in a synthesis photographing area 330, can be obtained.

The first radiation imaging device D1 on the upper level is positioned and retained by first retainers 301 and second retainers 302. The second retainers 302 are positioned to retain the lower corners of the first radiation imaging device D1. The second retainers 302 are provided for retaining the first radiation imaging device D1 from below, and for positioning and retaining the first radiation imaging device D1 in the front-back direction. For positioning of the first radiation imaging device D1 in the lateral (horizontal) direction, the first retainers 301 retain side portions of the first radiation imaging device D1 in the lateral (horizontal) direction. The side portions correspond to portions outside the effective pixel area of the radiation imaging device, and correspond to the effective photographing area indicated by the index 208 on the door unit 202. The effective pixel area of the radiation imaging device corresponds to an area where a plurality of pixels for acquiring a photographed image in the radiation detecting panel 2 are arranged in a two-dimensional matrix. The first retainers 301 each have a rail groove for retaining the first radiation imaging device D1. The first radiation imaging device D1 is mounted by sliding it downward along rails. Each of the retainers 301 and 302 is not disposed on the irradiated side of the effective pixel area of any of the radiation imaging devices D1, D2, and D3, and is disposed in an area other than the irradiated side of the effective pixel area. Specifically, the first retainers 301 are disposed only outside the effective pixel area of the first radiation imaging device D1 in the lateral direction. The second retainers 302 are disposed only outside the effective pixel areas of the first radiation imaging device D1 and the second radiation imaging device D2 in the lateral direction. With this configuration, each retainer can be prevented from appearing in the photographed image.

The second radiation imaging device D2 in the middle is retained by third, fourth, and fifth retainers 311, 312, and 313. The third retainers 311 and the fourth retainers 312 each have a rail groove for retaining the second radiation imaging device D2. The second radiation imaging device D2 is mounted by laterally sliding it along rails. By passing the second radiation imaging device D2 through the opening of one of the handles 207 described with reference to FIGS. 2A to 2C, the second radiation imaging device D2 can be operated from the side without retracting the handle 207. The fifth retainer 313 also serves as a portion to be contacted when the second radiation imaging device D2 is mounted by sliding it along the rails. The fifth retainer 313 thus retains the second radiation imaging device D2 to laterally regulate its position. As necessary, a pressing mechanism may be provided to ensure reliable contact with the fifth retainer 313. Each of the retainers 311, 312, and 313 is not disposed on the irradiated side of the effective pixel area of any of the radiation imaging devices D1, D2, and D3, and is disposed in an area other than the irradiated side of the effective pixel area. With this configuration, each retainer can be prevented from appearing in the photographed image. Specifically, the third retainers 311 are disposed opposite the irradiated side of the effective pixel area of the first radiation imaging device D1, and only to the upper side of (outside) the effective pixel area of the second radiation imaging device D2. The fourth retainers 312 are disposed opposite the irradiated side of the effective pixel area of the third radiation imaging device D3, and only to the lower side of (outside) the effective pixel area of the second radiation imaging device D2. The fifth retainer 313 is disposed only outside the effective pixel area of the second radiation imaging device D2 in the lateral direction.

The third radiation imaging device D3 on the lower level is retained by sixth retainers 321 and a seventh retainer 322. For positioning of the third radiation imaging device D3 in the lateral (horizontal) direction, the sixth retainers 321 retain side portions of the third radiation imaging device D3 in the lateral (horizontal) direction. The sixth retainers 321 each have a rail groove for retaining the third radiation imaging device D3. The third radiation imaging device 133 is mounted by sliding it downward along rails. The seventh retainer 322 is disposed to retain the lower side portion of the third radiation imaging device D3. The seventh retainer 322 serves as a lower supporting portion that retains the third radiation imaging device D3 from below. Each of the sixth retainers 321 and the seventh retainer 322 is not disposed on the irradiated side of the effective pixel area of any of the radiation imaging devices D1, D2, and D3, and is disposed in an area other than the irradiated side of the effective pixel area. Specifically, the sixth retainers 321 are disposed only outside the effective pixel area of the third radiation imaging device D3 in the lateral direction. The seventh retainer 322 is disposed only to the lower side of (outside) the effective pixel area of the third radiation imaging device D3. With this configuration, each retainer can be prevented from appearing in the photographed image.

That is, the retainers described above are configured to retain the plurality of radiation imaging devices in areas other than the effective pixel areas of the radiation imaging devices. The retainers that retain the second radiation imaging device D2 disposed opposite the irradiated side of the first radiation imaging device D1 may be disposed opposite the irradiated side of the first radiation imaging device D1. However, the retainers that retain the second radiation imaging device D2 need to be disposed in areas other than the irradiated side of the effective pixel area of the second radiation imaging device D2. On the other hand, the retainers that retain the first radiation imaging device D1 disposed closer to the irradiation side than the second radiation imaging device D2 is need to be disposed in areas other than the irradiated sides of the effective pixel areas of both the first and second radiation imaging devices D1 and D2.

In the configuration described above, any of the retainers is disposed in an area other than the irradiated sides of the effective pixel areas of the radiation imaging devices D1, D2, and D3. Thus, each retainer can be prevented from appearing in the photographed image, and the photographed image with no quality loss can be obtained. The radiation imaging devices are mounted in different ways, so that the operator can easily mount them without leaning forward or moving the container 201 up and down. The burden on the operator can thus be reduced.

Figure 4A:
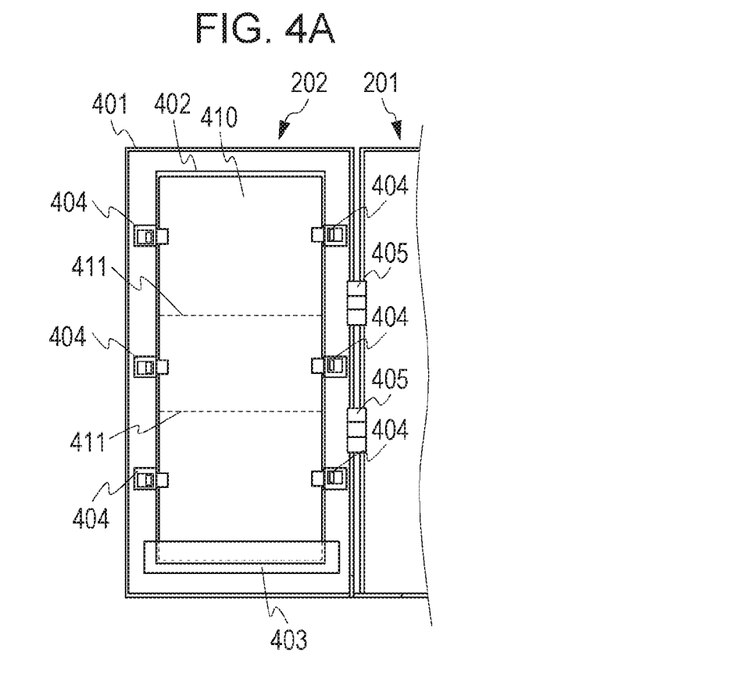
FIGS. 4A and 4B illustrate a configuration of a door unit according to an aspect of the present invention.
Figure 4B:
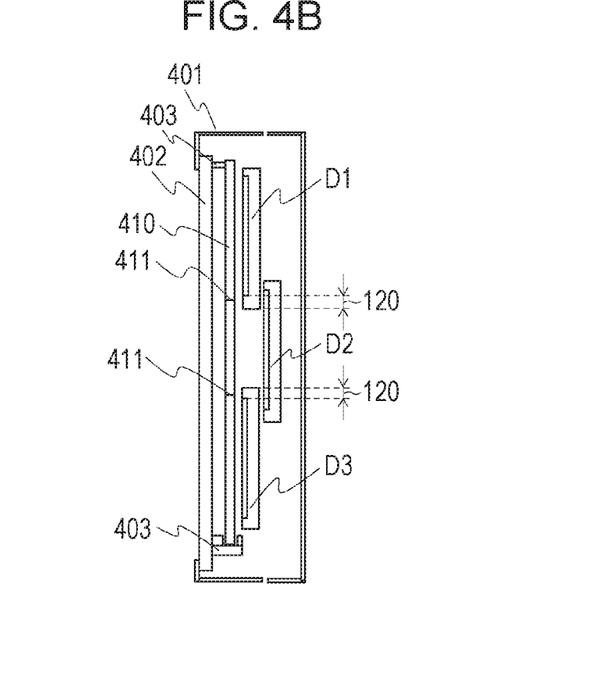

FIGS. 4A and 4B illustrate a configuration of the door unit 202. FIG. 4A illustrates the door unit 202 in an open state, as viewed from the inside of the door unit 202. FIG. 4B is a cross-sectional side view of the door unit 202 in a closed state.

The door unit 202 is formed by attaching a top panel 402 and a grid 410 for eliminating scattered radiation to a frame 401. The frame 401 is made of metal, such as iron, and attached to the container 201 with hinges 405. The frame 401 has an opening on its front side, to which the top panel 402 transmitting more radiation than the frame 401 is attached. For example, an acrylic or CFRP plate is used as the top panel 402. The grid 410 is attached to the frame 401 by using a grid base 403 attached to the frame 401 and holding the grid 410, and also by using grid securing portions 404 for securing the frame 401. The grid 410 is deformed when under a heavy load, and this causes artifacts in a radiographic image. To prevent this, the grid 410 is held at a position spaced from the top panel 402. Therefore, even if the top panel 402 is warped under an external load, no significant load is placed on the grid 410. A grid with a different property may need to be used for each photographing, depending on the area to be photographed. For this, the grid 410 is configured to be detachable from the frame 401. Specifically, the grid securing portions 404 are configured to be laterally slidable, so that the grid 410 can be detached from the grid base 403 by retracting the grid securing portions 404. It is difficult to complete the longitudinal production of the grid 410 in a single step. Accordingly, the grid 410 is produced by putting smaller-sized grids together in the longitudinal direction while forming seams 411 where a plurality of grids overlap each other. The seams 411 slightly appear in the radiographic image, and form areas where artifacts occur. The grid 410 is disposed such that the seams 411 spatially overlap the corresponding areas 120. As described above, the areas 120 are areas where image quality is degraded. Accordingly, by making the seams 411 where artifacts occur coincide with the areas 120, the proportion of the low quality region in the entire photographed image can be reduced. Although the grid 410 produced by putting smaller-sized grids together has been described here, a structure that can accommodate three smaller-sized grids may be provided. By using a plurality of grids generally used, it is possible to eliminate the need for preparing a new grid, and thus to achieve cost reduction.

Figure 5A:
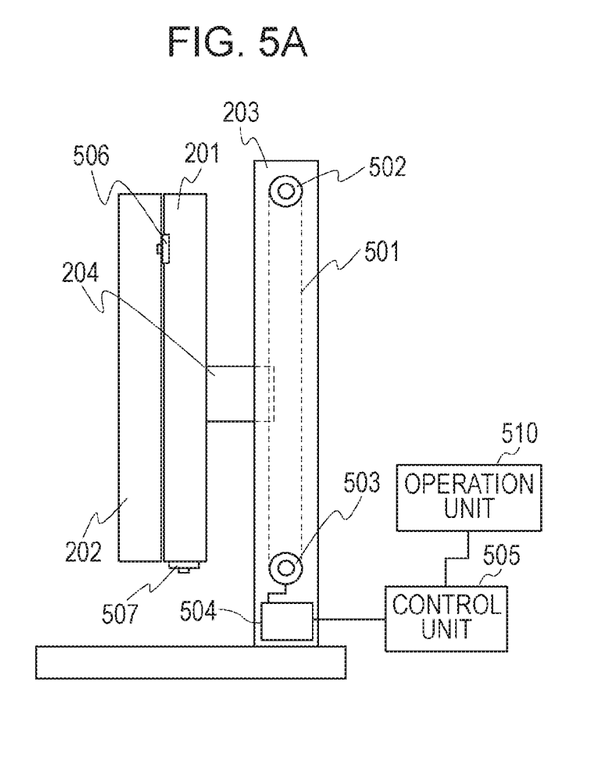
FIGS. 5A and 5B illustrate a function for up-and-down movement of a container according to an aspect of the present invention.
Figure 5B:
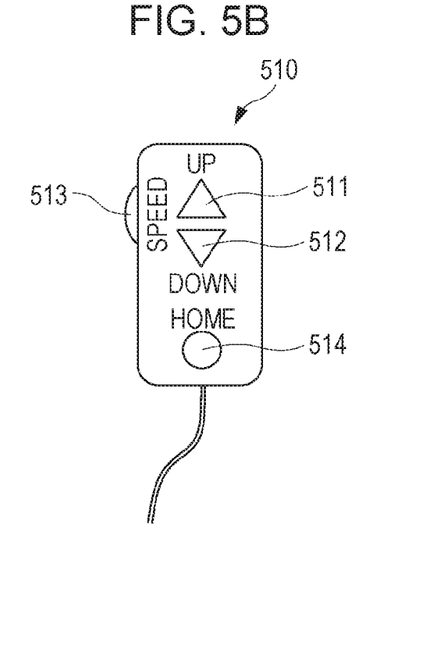

FIGS. 5A and 5B illustrate a function for up-and-down movement of the container 201. FIG. 5A is a schematic cross-sectional side view, and FIG. 5B illustrates an operation unit.

The supporting column 203 includes a chain 501, gears 502 and 503, and a drive unit 504. The drive unit 504 rotates the gear 503, and the rotation of the gear 503 is transmitted to the chain 501 to move the chain 501 up and down. Since the chain 501 is connected to the connecting portion 204, the container 201 can be moved up and down by the operation of the drive unit 504. For example, the drive unit 504 includes a motor and a speed reducer. The drive unit 504 is connected to a control unit 505, by which the direction and speed of the up-and-down movement are controlled. The control unit 505 is connected to an operation unit 510, which allows the user to input a desired operation. The operation unit 510 includes operation portions 511 and 512 for the up-and-down movement, an operation portion 513 for adjusting the speed of the up-and-down movement, and an operation portion 514 for returning to a predetermined home position. The home position is, for example, a position which allows an easy mounting operation, or a position which allows photographing of an adult of typical height. The container 201 is provided with switches 506 and 507. The switches 506 and 507 are connected to the control unit 505, and operate as an interlock for the up-and-down movement when the door unit 202 is not closed, the switch 506 transmits a control signal to the control unit 505 to prevent the up-and-down movement. If the switch 507 comes into contact with an obstacle under the container 201, the switch 507 transmits a control signal to the control unit 505 to prevent the up-and-down movement. For example, if a foot gets caught, the up-and-down movement is automatically stopped, so that safety can be ensured.

Figure 6A:
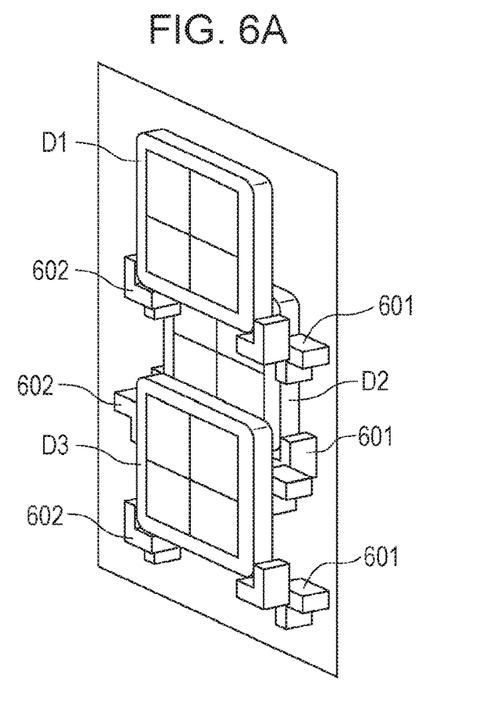
FIGS. 6A to 6D illustrate a modification of the radiation imaging devices for long-length photographing.
Figure 6B:
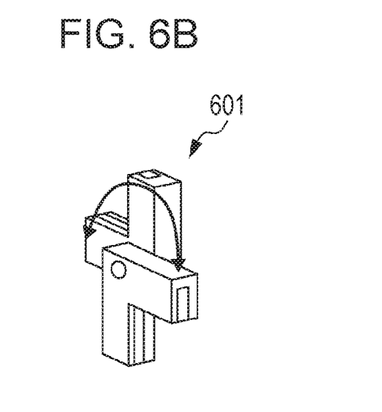
Figure 6C:
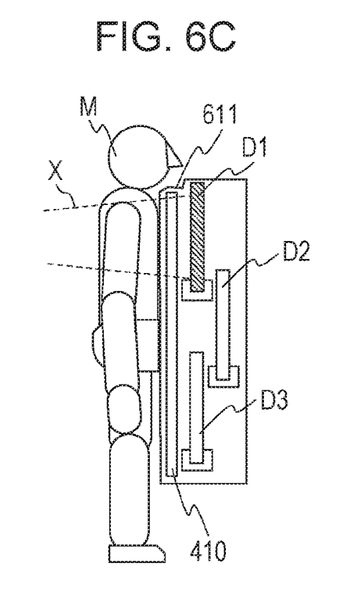
Figure 6D:
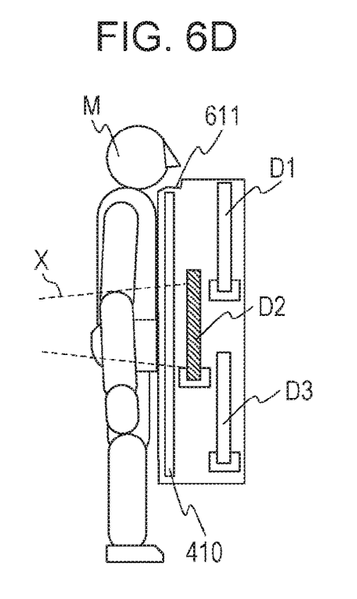

A modification of the radiation imaging devices for long-length photographing will now be described with reference to FIGS. 6A to 6D. FIG. 6A illustrates a mounted state of the radiation imaging devices D, FIG. 6B illustrates a retainer for the radiation imaging devices D, and FIGS. 6C and 6D illustrate usage patterns in the present modification.

Eighth retainers 601 and ninth retainers 602 are positioned to retain the corresponding lower corners of the radiation imaging devices D1, D2, and D3. As illustrated in FIG. 6B, the eighth retainers 601 and the ninth retainers 602 are each 180-degree rotatable in a plane parallel to the radiation incidence plane of each radiation imaging device, and can provide two modes: a mode of mounting the radiation. imaging device on the front side, and a mode of mounting the radiation imaging device on the back side. It is thus possible to change the overlapping order of the radiation imaging devices D1, D2, and D3 from the irradiation side. For example, as illustrated in FIG. 6C, if the first radiation imaging device D1 alone is used to photograph only the chest of a subject M, a better image can be obtained when the first radiation imaging device D1 and the subject M are closer to each other. Accordingly, the first radiation imaging device D1 is mounted on the front side in this case. For example, as illustrated in FIG. 6D, if the second radiation imaging device D2 alone is used to photograph only the abdomen of the subject F, a better image can be obtained when the second radiation imaging device D2 and the subject M are closer to each other. Accordingly, the second radiation imaging device D2 is mounted on the front side in this case. In the present configuration, the retainers for the first radiation imaging device D1 on the upper level are provided only on the lower side. This reduces the amount of lifting of the first radiation imaging device D1, and can reduce the distance between the first radiation imaging device D1 and the upper surface of the housing. With a chin rest 611, an area above the chest can be photographed. The eighth retainers 601 and the ninth retainers 602 are each positioned in an area other than the irradiated sides of the effective pixel areas of the radiation imaging devices D1, D2, and D3. Thus, each retainer can be prevented from appearing in the photographed image, and the photographed image with no quality loss can be obtained.

Figure 7A:
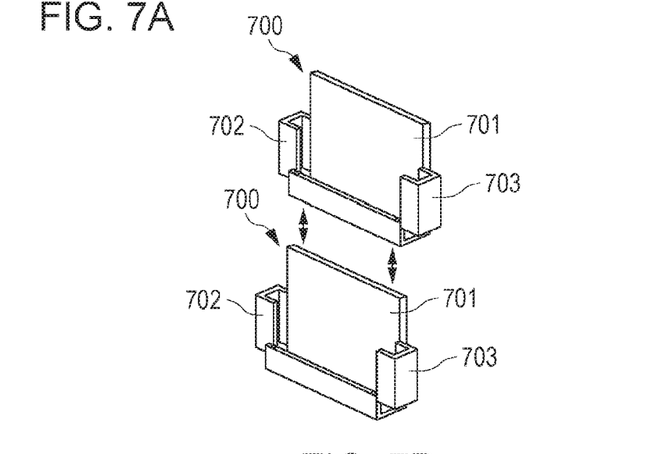
FIGS. 7A to 7C illustrate another modification of the radiation imaging devices for long-length photographing.
Figure 7B:
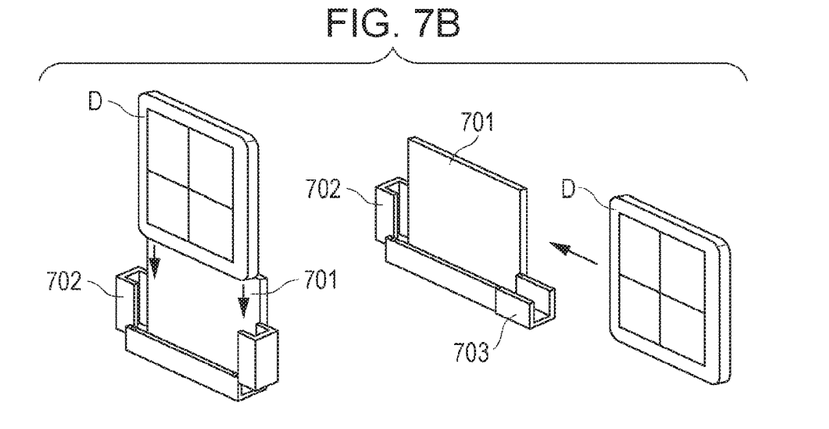
Figure 7C:
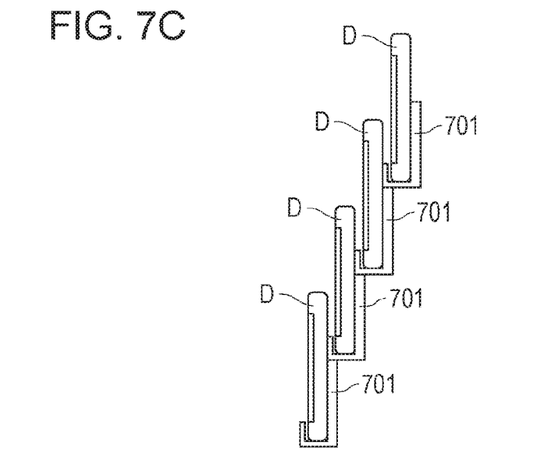

Another modification of the radiation imaging devices for long-length photographing will now be described with reference to FIGS. 7A to 7C. FIG. 7A illustrates a coupling structure of retainers for the radiation imaging devices D, FIG. 7B illustrates how the radiation imaging devices D are secured, and FIG. 7C illustrates how the radiation imaging devices D are mounted.

A tenth retainer 700 includes a back-side retaining member 701 formed by a back plate and a lower-side supporting portion, and also includes side retaining members 702 and 703 for positioning in the lateral direction. The back-side retaining member 701 and the side retaining members 702 and 703 are secured with hinges. Each of the radiation imaging devices D can be mounted by sliding it downward. Alternatively, by causing the side retaining member 702 or 703 to pivot 90 degrees using the hinge, the radiation imaging device D can be mounted by laterally sliding it. A plurality of tenth retainers 700 can be coupled to each other in the longitudinal direction. By preparing a plurality of tenth retainers 700, an area of any length can be photographed. Each of the tenth retainers 700 is positioned in an area other than the irradiated side of the effective pixel area of each radiation imaging device D. Thus, the tenth retainer 700 can be prevented from appearing in the photographed image, and the photographed image with no quality loss can be obtained.

Figure 8A:
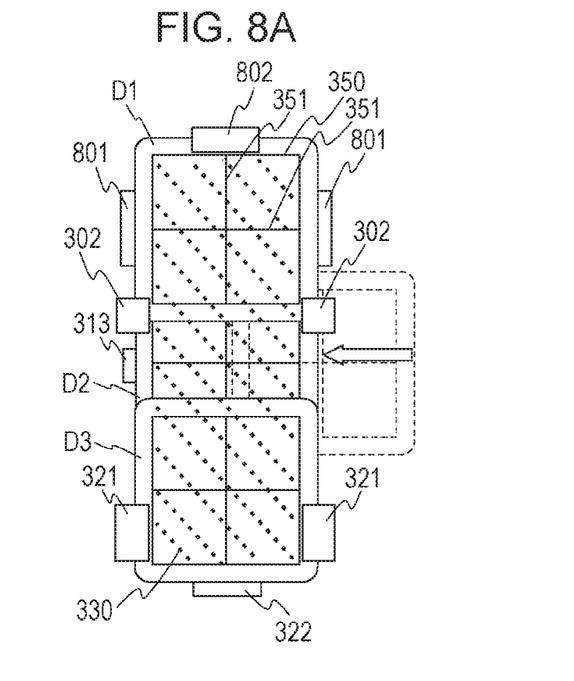
FIGS. 8A and 8B illustrate another modification of the radiation imaging devices for long-length photographing.
Figure 8B:
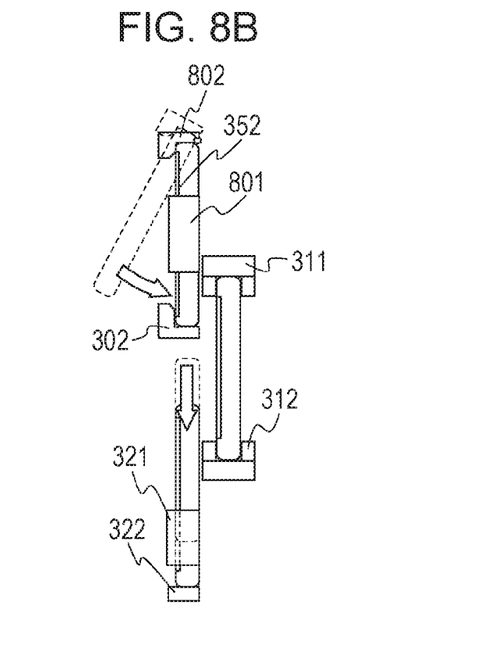

Another modification of the radiation imaging devices for long-length photographing will now be described with reference to FIGS. 8A and 8B. FIG. 8A is a front view, and FIG. 8B is a side view. The same components as those described with reference to FIGS. 3A and 3B will be denoted by the same reference numerals and their detailed description will be omitted.

The present modification differs from the configuration described with reference to FIGS. 3A and 3B in the following respects. First of all, first retainers 801 are disposed only outside the effective pixel area of the first radiation imaging device D1 in the lateral direction. For positioning of the first radiation imaging device D1 in the lateral (horizontal) direction, the first retainers 801 retain side portions of the first radiation imaging device D1 in the lateral (horizontal) direction. A third retainer 802 is added here. On the top of the first radiation imaging device D1, the third retainer 802 suppresses the movement of the first radiation imaging device D1 from the front. The third retainer 802 is positioned to retain an upper side portion of the first radiation imaging device D1. The third retainer 802 is provided for retaining the first radiation imaging device D1 from the upper side, and for positioning and retaining the first radiation imaging device D1 in the front-back direction. The third retainer 802 is configured to be retractable from a position for retaining the first radiation imaging device D1, so that the first radiation imaging device D1 can be mounted or removed. Specifically, after the first radiation imaging device D1 is placed away from the position for retaining the first radiation imaging device D1, the third retainer 802 moves the first radiation imaging device D1 in the direction of an arrow shown in FIG. 8B. Then, the lower side of the first radiation imaging device D1 is retained by the second. retainers 302 and the side portions of the first radiation imaging device D1 in the lateral (horizontal) direction are retained by the first retainers 801, whereby the first radiation imaging device D1 is mounted in place.

With the configuration described above, the first radiation imaging device D1 on the upper level and the third radiation imaging device D3 on the lower level can be mounted in the container 201 from the front of the retainers (i.e., from the irradiation side). On the other hand, the second radiation imaging device 02 in the middle can be mounted in the container 201 from the side of the retainers. As described above, the radiation imaging devices on the upper and lower levels and the radiation imaging device in the middle are mounted in different ways, so that the operator can easily mount them without leaning forward or moving the container 201 up and down. Thus, as compared to the example illustrated in FIGS. 3A and 3B, the burden on the operator can be further reduced.

While the present invention has been described with reference to embodiments, it is to be understood that the invention is not limited to the disclosed embodiments.

This application claims the benefit of Japanese Patent Application No. 2015-017883 filed Jan. 30, 2015 and No. 2015-162919 filed Aug. 20, 2015, which are hereby incorporated by reference herein in their entirety.

What is claimed is:

1. A radiation imaging system comprising:
    a housing containing a plurality of radiation imaging devices, each radiation imaging device including a radiation detecting panel having a two-dimensional matrix of pixels and arranged to convert applied radiation to an image signal;
    a plurality of retainers configured to position and retain the plurality of radiation imaging devices so that parts of the plurality of radiation imaging devices spatially overlap as viewed from an irradiation side; and
    a radiographing controller configured to acquire a radiographic image on the basis of image signals from the plurality of radiation imaging devices,
    wherein the plurality of retainers are configured to retain the plurality of radiation imaging devices in areas other than effective pixel areas of the plurality of radiation imaging devices.

2. The radiation imaging system according to claim 1, wherein the plurality of retainers are disposed only in areas other than irradiated sides of the effective pixel areas of the plurality of radiation imaging devices.

3. The radiation imaging system according to claim 2, wherein the plurality of radiation imaging devices include a first radiation imaging device and a second radiation imaging device;
of the plurality of retainers, a retainer retaining the second radiation imaging device disposed opposite an irradiated side of the first radiation imaging device is disposed only in an area other than the irradiated side of the effective pixel area of the second radiation imaging device; and
of the plurality of retainers, a retainer retaining the first radiation imaging device is disposed only in an area other than the irradiated side of the effective pixel area of the first radiation imaging device and an area other than the irradiated side of the effective pixel area of the second radiation imaging device.

4. The radiation imaging system according to claim 3, wherein the retainer retaining the second radiation imaging device is disposed opposite the irradiated side of the effective pixel area of the first radiation imaging device.

5. The radiation imaging system according to claim 4, wherein the plurality of radiation imaging devices include a third radiation imaging device disposed closer to the irradiation side than the second radiation imaging device is; and
the plurality of retainers are configured to position and retain the plurality of radiation imaging devices such that the third radiation imaging device is disposed lower than the first radiation imaging device and the second radiation imaging device, and that the first radiation imaging device is disposed higher than the second radiation imaging device.

6. The radiation imaging system according to claim 5, wherein the first radiation imaging device is retained by a first retainer and a second retainer of the plurality of retainers;
the first retainer retains a side portion of the first radiation imaging device in a lateral direction for positioning of the first radiation imaging device in the lateral direction; and
the second retainer retains a lower corner of the first radiation imaging device.

7. The radiation imaging system according to claim 6, wherein the second radiation imaging device is retained by a third retainer, a fourth retainer, and a fifth retainer of the plurality of retainers;
the third retainer is disposed only opposite the irradiated side of the effective pixel area of the first radiation imaging device and above the effective pixel area of the second radiation imaging device;
the fourth retainer is disposed only opposite the irradiated side of the effective pixel area of the third radiation imaging device and below the effective pixel area of the second radiation imaging device; and
the fifth retainer is disposed only outside the effective pixel area of the second radiation imaging device in the lateral direction.

8. The radiation imaging system according to claim 7, wherein the third radiation imaging device is retained by a sixth retainer and a seventh retainer of the plurality of retainers;
the sixth retainer is disposed only outside the effective pixel area of the third radiation imaging device in the lateral direction; and
the seventh retainer is disposed only below the effective pixel area of the third radiation imaging device.

9. The radiation imaging system according to claim 5, wherein the first radiation imaging device and the third radiation imaging device are mounted from the irradiation side, which is the front of the plurality of retainers, into the housing, and the second radiation imaging device is mounted from a side of the plurality of retainers into the housing.

10. The radiation imaging system according to claim 3, wherein an overlapping order of the plurality of radiation imaging devices from the irradiated side can be changed.

11. The radiation imaging system according to claim 10, wherein the plurality of retainers are each configured so as to be rotatable in a plane parallel to radiation incidence planes of the plurality of radiation imaging devices.

12. The radiation imaging system according to claim 1, wherein the housing comprises a grid for eliminating scattered radiation, and the grid has a seam formed by arranging a plurality of smaller grids together in a longitudinal direction, and the seam is positioned to spatially overlap an overlapping portion of two of the plurality of radiation imaging devices.

13. The radiation imaging system according to claim 1, wherein the housing has an index to make a position of an overlapping portion of two of the plurality of radiation imaging devices externally visible.

14. The radiation imaging system according to claim 1, wherein the housing has an index to make an effective photographing area externally visible, the effective photographing area corresponding to the effective pixel area of each of the plurality of radiation imaging devices as viewed from a predetermined radiation source.

15. The radiation imaging system according to claim 1, wherein the housing has a display unit for displaying a state of each of the plurality of radiation imaging devices.

16. The radiation imaging system according to claim 1, wherein, of the plurality of radiation imaging devices, a first radiation imaging device disposed in front of a second radiation imaging device, as viewed from the irradiation side, includes a radiation shielding member on a back side of the radiation detecting panel; and
the radiation shielding member is disposed so as not to spatially overlap the effective pixel area of the second radiation imaging device.

17. The radiation imaging system according to claim 16, wherein, of the plurality of radiation imaging devices, a third radiation imaging device disposed lower than the first radiation imaging device and the second radiation imaging device and in front of the second radiation imaging device, as viewed from the irradiation side, includes a radiation shielding member on a back side of the radiation detecting panel; and
the radiation shielding member is disposed so as not to spatially overlap the effective pixel area of the second radiation imaging device.

18. The radiation imaging system according to claim 16, wherein the radiation shielding member is disposed in the same area as an effective pixel area of the radiation detecting panel in the first radiation imaging device, or in an area inside the effective pixel area of the radiation detecting panel.

19. A radiation imaging system comprising:
a plurality of retainers configured to position and retain a plurality of radiation imaging devices, each radiation imaging device including a radiation detecting panel having a two-dimensional matrix of pixels and configured to convert applied radiation to an image signal, such that parts of the plurality of radiation imaging devices spatially overlap as viewed from an irradiation side; and a radiographing controller configured to acquire a radiographic image on the basis of image signals from the plurality of radiation imaging devices, wherein at least a part of each of the plurality of retainers is configured to retain a corresponding one of the plurality of radiation imaging devices in an area other than effective pixel areas of the plurality of radiation imaging devices, as viewed from the irradiation side.

20. A radiation imaging device used in a radiation imaging system including a plurality of retainers configured to position and retain a plurality of radiation imaging devices, each radiation imaging device including a radiation detecting panel having a two-dimensional matrix of pixels and configured to convert applied radiation to an image signal, such that parts of the plurality of radiation imaging devices spatially overlap as viewed from an irradiation side, the radiation imaging system further including a radiographing controller configured to acquire a radiographic image on the basis of image signals from the plurality of radiation imaging devices, the radiation imaging device comprising a unit configured to be retained by a corresponding retainer in an area other than an effective pixel area of the radiation imaging device as viewed from the irradiation side.

* * * * *